United States Patent [19]

Teague

[11] 4,393,868
[45] Jul. 19, 1983

[54] COLLES FRACTURE FIXATURE DEVICE

[75] Inventor: H. Derek Teague, Manhattan Beach, Calif.

[73] Assignee: Ace Orthopedic Manufacturing Inc., Los Angeles, Calif.

[21] Appl. No.: 236,267

[22] Filed: Feb. 20, 1981

[51] Int. Cl.³ .............................................. A61F 5/04
[52] U.S. Cl. .................................. 128/92 A; 128/92 B
[58] Field of Search ................ 128/92 A, 84 B–84 C, 128/92 B; 403/57, 79, 157

[56] References Cited

U.S. PATENT DOCUMENTS

| 2,214,490 | 9/1940 | Thomas | 128/84 B |
| 2,371,519 | 3/1945 | Haynes | 128/92 A |
| 2,391,537 | 12/1945 | Anderson | 128/84 B |
| 4,220,146 | 9/1980 | Cloutier | 128/92 A |
| 4,244,360 | 1/1981 | Dohogne | 128/92 A |

FOREIGN PATENT DOCUMENTS 740241  6/1980  U.S.S.R. ............................ 128/92 A

*Primary Examiner*—Kyle L. Howell
*Assistant Examiner*—C. W. Shedd
*Attorney, Agent, or Firm*—Hubbard & Stetina

[57] ABSTRACT

A Colles fracture fixature device comprised of a pair of curved, slotted frame members for received fixation pin holders having a pin bushing rotatably received in the bore of the fork arms of a clevis.

1 Claim, 6 Drawing Figures

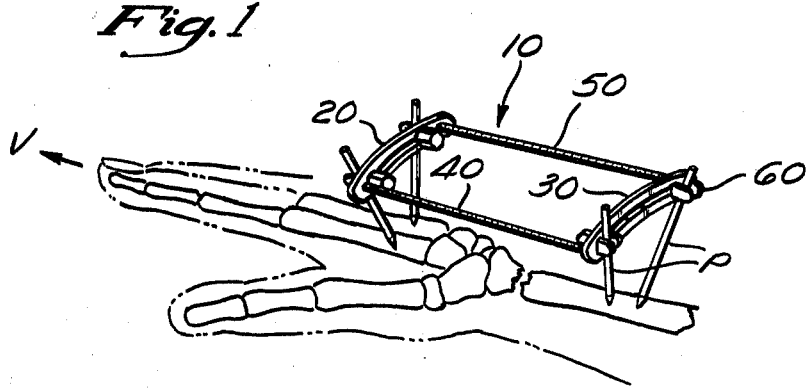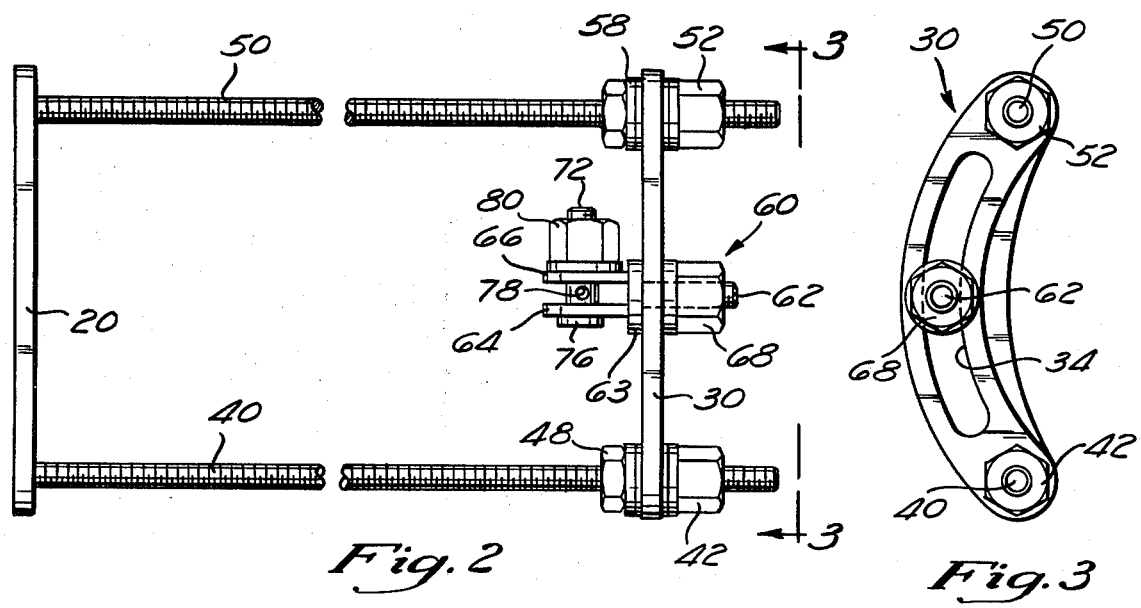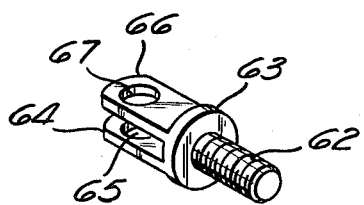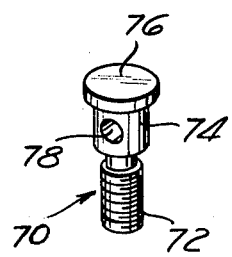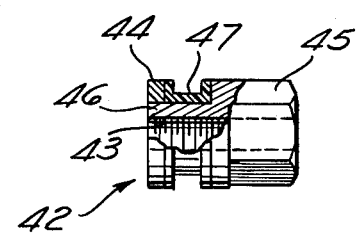

COLLES FRACTURE FIXATURE DEVICE

TECHNICAL FIELD

This invention relates to orthopedic external fixation apparatus generally with particular applicability to external fixature for stabilizing a Colles fracture.

BACKGROUND ART

A Colles fracture is a fracture of the forearm radius bone close to the wrist joint. In treating such a fracture, the physician must manipulate the two halves of bone on either side of the fracture back together to form a stable volar buttress. Once the two bond halves are mated, they must be fixed together for a period long enough for the bones to mend.

Various devices are known in the prior art for external fixation of bone fractures. For example, U.S. patent application Ser. No. 085,996, filed on Oct. 18, 1979, discloses an external fixature device comprised of longitudinal, adjustable length frame members held in parallel by semicircular frame members which have a plurality of holes in them for receiving fixation pin clamps. Because hooks and not slots are used, the combination of relative angles of the pins one to the other and spacing of the pins from each other are not continuously variable and therefore there are less than an infinite number of combinations. U.S. Pat. No. 1,789,060 discloses a bond fracture clamp utilizes four pins which are drilled and tapped into the bone halves and which are themselves externally stabilized by a framework divided into two halves and connected in the center by a ball and socket joint. This joint may be manipulated to the proper position and locked in place.

Russian Pat. No. 560,605 shows a device using two pins wherein each pin is passed completely through one of the bone halves and out from the other side of the limb. The pins are attached to semicircular slotted frames by adjustable couplings such that their angle relative to each other can be changed. These semicircular couplings themselves are connected via rods which are connected to each end of the semicircle, and to an X-like frame structure which pivots at its intersection point.

U.S. Pat. No. 4,003,340 teaches a surgical compression instrument with an outer ring having longitudinal connecting members with a smaller ring inside connected to the larger ring by radial coupling members. The smaller ring has clamps for fixature needles which are passed completely through the bone fragment on either side of the fracture. The radial couplers are threaded so that the inner ring can move in any direction and turn within the outer ring. The inner ring can also be positioned in a plane turned at an angle with respect to the plane of the outer ring.

Russian Pat. No. 591,182 discloses a device for aligning the head with the hip such that spinal injuries may be treated. The device teaches a semicircular slotted frame at the top having pins which can be screwed into the scalp. The semicircular fixture is connected by vertical rods to a hip device which fits around the pelvic region of the patient and has pins which are surgically passed through the pelvic bone to stabilize it. The three vertical rods passing through the semicircular fixture about the head pass through slots and that fixture can be clamped such that the fixture, once clamped to the skull, can then be twisted to orient the head and spine in the proper direction and then clamped to prevent any further movement.

U.S. Pat. No. 3,727,610 teaches a fixation device for a diaphyses fracture. The device comprises two fixation pins which are clamped to semicircular frame devices having slots therein such that the angles of the pins relative to each other can be varied and permanently clamped. Two pins are attached to each of the semicircular frame devices and passed completely through the bone and limb. The two semicircular frame members are connected to each other by threaded rods and couplings such that their longitudinal distance from each other can be varied.

U.S. Pat. No. 3,997,397 discloses a device comprised of several circular rings having pins clamped to said rings which pass entirely through bone segments. The rings are connected to each other by springs such that once the pins are passed through the bone fragments, the springs will keep the fragments together by applying compression forces thereto.

The well-known Roger Anderson device is designed for reducing unstable Colles fractures. The Roger Anderson device consists of two unthreaded rods which are placed on the forearm over the fracture site. Four knuckle joints, which hold fixation pins, are slidably connected to the rods so that they may be inserted into the radius bone on the elbow side of the fracture and into the second and third metacarpal bones on the hand side of the fracture. After the fracture is reduced, the physician inserts the pins and slides the knuckle joints to the proper position and clamps them down. The upper portions of the pins are coupled via crossed members and knuckle joints such that the angle of the pins with respect to each other can be changed and clamped. The disadvantage of this device is that eight knuckle joint type clamps are involved in the process of clamping the fracture. Two persons may be required in setting the fracture, i.e., one person holding the bones in correct orientation while the other person manipulates the pins, knuckle joints, and connecting rods and clamp screws. The complexity and physical dexterity required renders this device difficult to use. In addition, the stability of the device leaves something to be desired if any one of the clamps becomes loose. If any clamp device loosens, the entire parallel piped structure may be weakened thereby altering the compressive forces applied to the fracture location. Also, the compressive forces in the fracture area are obtained by manually pressing the bone halves together to the desired compressive level, then sliding the knuckle joints holding the pins inserted into the bones to positions required to maintain the compressive force. Then all knuckle joints must be tightened to maintain compression.

STATEMENT OF THE INVENTION

The external fixation device provides a compact, light, versatile and yet very rigid means for fixing the position of surgical fixation pins, the angular orientation thereof and the extent longitudinally of surgical pins from the fixation device to provide an extremely rigid fixation of bone fragments during healing, and includes means for reducing bone fractures by moving the bone fragments longitudinally together in butting relationship and holding them in such position during healing.

The external fixation device of this invention comprises at least two elongate rigid spaced support members which have openings therethrough generally arcuately in the form of a slot extending proximate one end to proximate the other end of the support member. Spacing means are provided to fix the support members in relatively spaced relationship. Fixation pin support means are connected to the respective spaced support members. The fixation pin support means include a connector portion which extends through the opening in the respective spaced support member, securing means for fixing the angular orientation of the pin support means on the spaced support member, and clamping means for clamping conventional surgical fixation pins securely, the securing and clamping means together fixing the angular orientation and the longitudinal extent of the surgical fixation pin relative to the respective spaced support member, the position of the fixation pin support means as fixed on the spaced support member determining the necessary angular orientation of the surgical fixation pin.

The spacing means, in the preferred embodiment, includes means for adjusting the space between the support members, thereby permitting movement of bone fragments toward each other for reduction of the fracture and for holding the bone fragments in firm, butting relationship, and adjusting the force between the bone fragments. Also in the preferred embodiment, the space support members are generally arcuately configured and the openings therethrough are generally arcuate slots.

The surgical fixation pin support means, in the preferred form of the invention, comprises a clevis which includes a pair of apertured spaced clamping members secured to the connector portion, which connects the surgical fixation pin support to the spaced support member. A clevis pin extends through the apertures in the clamping members, the clevis pin having a passage therethrough which is adapted to snuggly receive the shaft of a conventional surgical fixation pin. The space between the clamping members of the clevis is slightly larger than the diameter of surgical fixation pin. Means are provided for pulling the clevis pin through the apertures in the clamping members thereby clamping the surgical fixation pin tightly in the passage in the clevis pin and between the clamping members of the clevis, thereby securely fixing the longitudinal extent of the surgical fixation pin of the fixation device.

The present invention constitutes an external fixation device for use in orthopedic surgery for fixing the angular orientation and longitudinally extent of surgical fixation pins which are adapted, when the device is in use, to be secured to bone fragments for stabilizing the bone fragments during healing. The invention comprises the combination of a pair, or more, of rigid support members; a pair, or more, of spacing bolts and means on the spacing bolts for adjusting and for fixing the spacing between the support members, and a plurality of surgical fixation pin support means. Each of the rigid support members is generally arcuate in configuration and has a generally rectangular cross-section, the major dimension of the cross-section of which extends, when a device is in use, generally perpendicular to the axis of the bone to be stabilized, and has a pair of spaced apart holes, typically adjacent the ends thereof, extending therethrough, and also an arcuate slot formed therethrough from proximate one end to proximate the other end of the support member, the holes and the slot being formed through the cross-section of the support member perpendicular to the major dimension thereof, i.e., the center axis of the holes extending generally perpendicular to the bone to be stabilized and, similarly, a center axis of the slot at any given point also extending generally parallel to the bone to be stabilized. The surgical fixation pin support means each comprising a connector portion which typically extends through and is slidable in the slot of a support member and a clevis which includes a pair of space clamping members, each of which has an aperture formed therethrough and means cooperating with the connector portion for removably and adjustably securing the connector portion in the slot of the support member. A clevis pin, having formed therethrough an aperture which is adapted to receiving fixation pin, extends through the apertures in the clamping members with the aperture in the clevis pin being positioned between the clamping members. Means are provided on the clevis pin for tightening the clamping members together on a fixation pin which is received, in use, in the aperture in the clevis pin, to thereby fix, relative to the support member, the distance and angular orientation of the bone fragment to be stabilized. Typically one or more such surgical fixation pin support means is used for each bone fragment to be stabilized.

BRIEF DESCRIPTION OF THE DRAWINGS

FIG. 1 is a perspective view of the fixature device of this invention as applied to a Colles fracture;

FIG. 2 is a top view of the fixature device;

FIG. 3 is a sectional view of the fixature device taken along section lines 3—3 in the direction of the arrow, as shown in FIG. 2;

FIG. 4 is a view of the adjusting element, showing the self-lubricating grommet in cross-section;

FIG. 5 is a view of the clevis;

FIG. 6 is a view of the clevis pin.

DETAILED DESCRIPTION

The present invention is specially configured for use in the reduction of Colles fractures and the following description will describe the invention and such application; it will be understood, however, that the apparatus may be used in connection with the conventional surgical pins for the reduction of other types of fractures.

FIG. 1 depicts the external fixation device 10 of this invention as applied in the reduction of a Colles fracture. Reduction of the fracture is performed by applying a small distraction force in the direction of Vector following by manipulation of radius bone fragments to form a stable volar buttress. The external fixation device of this invention will be described in connection with this manipulation of the radius bone fragment.

The external fixation device of this invention, indicated generally at 10, comprises, typically a pair of rigid spaced support members 20 and 30. More than two support members may be used but typically only two sets of such support members will be used. Each of the rigid spaced support members has one or more openings therethrough extending between or spaced at intervals from proximate one end to proximate the other end of the support member. In the preferred form, each of the support members is generally arcuate in configuration and includes a slot also arcuate in configuration extending from proximate one end to proximate the other end of the support member. The arc configuration need not be circular.

The spaced support members are held in relatively spaced, generally parallel relationship with each other, by spacing means which extend between the support members. The spacing means 40 and 50 are the preferred form of such members, but are not limiting as to the scope of the invention.

At least one, and usually two, surgical fixation pin support means are secured to each of the respective spaced support members. Each surgical fixation pin support means comprises a connector portion which extends through the opening in the respective spaced support member, securing means for fixing the angular orientation of the pin support means on the spaced support member and clamping means clamping a surgical fixation pin, indicated at P in FIG. 1, securely, the securing and clamping means fixing the angular orientation and longitudinally extent of the surgical fixation pin relative to the respective spaced support member, when the fixation device is in use.

Details of the construction of an exemplary spaced support member are shown in FIGS. 2 and 3. The spaced support member 30, which is described as exemplary, comprises an elongate rigid element 32 which, in the preferred embodiment, is generally arcuately configured, as best shown in FIG. 3. One or more openings extend through the rigid arcuate spaced support member, as shown at 34, wherein the preferred embodiment of the slot, is depicted as an elongate slot, arcuate in configuration, extending from proximate one end to the support member to proximate the other end of the support member. Holes adjacent to respective ends of the rigid support member are provided through which the spacing bolts 40 and 50, and adjusting means 42 and 52, respectively, extend, as shown in FIGS. 2 and 3. The arcuate element 30 is approximately 3/32 inch in thickness, about 3 inches in length, with a slot of about 2 inches in length formed therein.

The member 20 is of like configuration, except that the holes are sized to receive rigidly press-fitted spacing rods 40 and 50. Spaced rigid support means having different curvatures may be used together.

The spacing rod 40 is an elongate linear threaded rod, the preferred embodiment between about 4 inches and about 8 inches in length, typically about 6 inches in length, preferably, rigidly secured at one end to the rigid support member 20 and extending through holes in the support member 30. The support member 30 is mounted on the rods 40 and 50 by means for adjusting the space between the support members 20 and 30, indicated generally at 42 and 52. Like adjusting means may be used to secure all rigid support members to the spacing means.

FIG. 4 depicts a detailed construction of the adjusting means 42. The adjusting means comprises a generally cylindrical body having a threaded aperture 43 formed therethrough, with a keeper ring 44 at one end and a wrench surface 45 at the other end, and a space 46 between the keeper ring and the wrench surface. A grommet 47, preferably of a self-lubricating polymer or copolymer, e.g., polyacetal impregnated with polytetrafluoroethylene, permits snug but free rotation of the adjusting means in the aperture of the support member. The wrench surface is typically in the form of a hexagonal nut of conventional construction. The aperture end of the rigid support member 30 is fitted into the slot 46, and the keeper ring 44 is pressed into place, securing the rigid support member 30 in the slot but permitting the adjusting element 42 to rotate therein. The adjusting element 42 is screwed on to the bolt 40 and can be adjusted longitudinally along the length of the threaded bolt 40 and can be locked at a specific point by means of the locking nut 48. The longitudinally adjusting means 52 is of like construction and is, similarly, movable along the threaded bolt 50 simply by turning it one direction or the other and can be locked into place by the lock nut 58.

The surgical fixation pin support means, at best shown in FIGS. 2, 5 and 6, comprises a connector portion 62, which extends through and is slidable in the slot 34 of the rigid spaced support member 30, and is likewise received in other rigid spaced support members. A clevis 63, including a pair of spaced clamp member 64 and 66 with apertures 65 and 67 therethrough, are secured to the connector portion. A nut 68, generally of the configuration of the portion 45 of the adjusting means, as shown in FIG. 4, provides means of securing the connector portion to the respective spaced support means in a fixed orientation. A clevis pin 7 which includes a threaded end 72, a central shaft portion 74 and a head 76, with an aperture 78 formed through the shaft, extends through the apertures in the clamping members of the clevis and is secured in place by a nut 80, preferably, the same type described with respect to nut 68, though any nut may be used in lieu of those shown at 68 and 80. Nut 80 provides means for pulling the clevis pin through the apertures and the clamping members, and, when the device is in ise with a pin P extending through the aperture 78, clamping the surgical fixation pin tightly in the passage in the clevis pin and tightly between the clamping members of the clevis, the combination of the securing means and the clamping means fixing the distance at the angle of extent of a surgical fixation pin from the respective spaced support member.

The external fixation device of this invention provides variable adjustment, and yet total rigidity. For example, the spacing between the surgical fixation pin longitudinally, the angle of orientation of the surgical fixation pin and the bone, and the entry point of the surgical fixation pin into the bone are completely within the discretion of the orthopedic surgeon, without any loss of rigidity or stability.

In use, the spacing between the rigid spaced support members is adjusted, by means of spacing means 42 and 52, to approximately that desired to locate the desired point of entry of the surgical fixation pins into the respective bones or bone fragments in the fracture. The fixation pins are secured into the bone in the conventional manner, and are secured loosely to the spaced support members by means of surgical fixation pin support means, which are wholly adaptable to the desired angle and point of entry of the surgical fixation pins. Any adjustment in the distance between the spacing along may, of course, be made at this stage. The surgical fixation pins are firmly secured to the rigid spaced support members and the pins are clamped in the surgical fixation pin support means, thereby rigidly affixing the relative relationship of all of the surgical fixation pins and, consequently, the relationship of the bone fragments of the fracture. If desired, the adjusting means may then be manipulated, simply by turning the nut heads formed thereon, for example the portion 45 of adjusting means 40, to force the ends of the bone fragments together. The amount of force exerted on the bones may be controlled by the amount of the rotation of the respective adjusting means 42 and 52. The position of the surgical fixation pin may be adjusted without affecting, in any degree, the rigidity and stability of the remainder of the external fixation device or any pins attached thereto. This capability presents a tremendous advantage over the known prior art devices.

It will now be clear that the present invention, as an overall combination, provides a degree of rigidity of support combined with ease of use and variable adjustment of individual pins not heretofore accomplished.

It will be understood that the foregoing description is of the exemplary embodiment and is not limiting to the scope of the invention being defined by the appended claims.

INDUSTRIAL APPLICATION

The device of this invention finds wide utilization in hospitals and by orthopedic surgeons throughout the world and is an item of significant value in commerce.

What is claimed is:

1. An external fixation device for use in orthopedic surgery for fixing the angular orientation and longitudinal extent of surgical fixation pins adapted, when in use, to be secured to bone fragments for stabilizing such bone fragments during healing, comprising, in combination:

a pair of rigid arcuate support members spaced apart from each other; each of the support members generally arcuate have a generally rectangular cross-section, the major dimension of which extends, in use, generally perpendicular to the axis of the bone to be stabilized; each support member has a hole proximate each end thereof; spaced from and positioned between said holes is an arcuate slot formed from proximate one hole to proximate the other hole, the holes and the slot being formed through the support member perpendicular to said major dimension thereof;

a pair of spacing bolts extending through the holes through the support members;

means on the spacing bolts for adjusting and for fixing the spacing between the support members;

a plurality of surgical fixation pin support means, each such pin support means comprising a connector portion extending from a clevis which includes a pair of spaced clamping members each of which has an aperture formed therethrough, means cooperating with the connector portion for removably and adjustably securing the pin support means in the slot of a support member, an elongated clevis pin having formed therethrough a transverse aperture which is adapted to receive a fixation pin; the clevis pin extends through the apertures in the clevis clamping members with the aperture in the clevis pin between said clamping members; and means on said clevis pin for tightening the clamping members together on a fixation pin received in the aperture in the clevis pin so that when the device is in use, the distance and angular orientation of the bone fragment to be stabilized is thereby fixed relative to the fixation device.

* * * * *

UNITED STATES PATENT AND TRADEMARK OFFICE
CERTIFICATE OF CORRECTION

PATENT NO. : 4,393,868
DATED : July 19, 1983
INVENTOR(S) : H. DEREK TEAGUE

It is certified that error appears in the above-identified patent and that said Letters Patent is hereby corrected as shown below:

Column 7, line 25, delete "generally arcuate".

Signed and Sealed this

Eighteenth Day of October 1983

[SEAL]

Attest:

GERALD J. MOSSINGHOFF

Attesting Officer     Commissioner of Patents and Trademarks